United States Patent
Chaubal et al.

(10) Patent No.: US 9,700,866 B2
(45) Date of Patent: Jul. 11, 2017

(54) SURFACTANT SYSTEMS FOR DELIVERY OF ORGANIC COMPOUNDS

(75) Inventors: Mahesh Chaubal, Lake Zurich, IL (US); Mark J. Doty, Grayslake, IL (US); Jamie T. Konkel, Island Lake, IL (US); Barrett E. Rabinow, Skokie, IL (US)

(73) Assignees: BAXTER INTERNATIONAL INC., Deerfield, IL (US); BAXTER HEALTHCARE SA, Glattpark (Opfikon) (CH)

( * ) Notice: Subject to any disclaimer, the term of this patent is extended or adjusted under 35 U.S.C. 154(b) by 1761 days.

(21) Appl. No.: 11/224,633

(22) Filed: Sep. 12, 2005

(65) Prior Publication Data

US 2006/0073199 A1 Apr. 6, 2006

Related U.S. Application Data

(63) Continuation-in-part of application No. 10/703,395, filed on Nov. 7, 2003, now Pat. No. 8,067,032, which is a continuation-in-part of application No. 10/390,333, filed on Mar. 17, 2003, now abandoned, which is a continuation-in-part of application No. 10/246,802, filed on Sep. 17, 2002, now abandoned, which is a continuation-in-part of application No. 10/035,821, filed on Oct. 19, 2001, now Pat. No. 6,977,085, which is a continuation-in-part of application No. 09/953,979, filed on Sep. 17, 2001, now Pat. No. 6,951,656, which is a continuation-in-part of application No. 09/874,637, filed on Jun. 5, 2001, now Pat. No. 6,869,617.

(60) Provisional application No. 60/258,160, filed on Dec. 22, 2000.

(51) Int. Cl.

| A61K 9/127 | (2006.01) |
|---|---|
| B01J 13/04 | (2006.01) |
| A61K 9/10 | (2006.01) |
| A61K 9/14 | (2006.01) |
| A61K 31/436 | (2006.01) |

(52) U.S. Cl.
CPC ............ B01J 13/04 (2013.01); A61K 9/10 (2013.01); A61K 9/1271 (2013.01); A61K 9/145 (2013.01); A61K 9/146 (2013.01); A61K 31/436 (2013.01)

(58) Field of Classification Search
None
See application file for complete search history.

(56) References Cited

U.S. PATENT DOCUMENTS

| 2,745,785 A | 5/1956 | Bruce et al. |
|---|---|---|
| 4,056,635 A | 11/1977 | Glen et al. |
| 4,073,943 A | 2/1978 | Wretlind et al. |
| 4,452,817 A | 6/1984 | Glen et al. |
| 4,540,602 A | 9/1985 | Motoyama et al. |
| 4,606,670 A | 8/1986 | Angell |
| 4,606,940 A | 8/1986 | Frank et al. |
| 4,608,278 A | 8/1986 | Frank et al. |
| 4,622,219 A | 11/1986 | Haynes |
| 4,725,442 A | 2/1988 | Haynes |
| 4,798,846 A | 1/1989 | Glen et al. |
| 4,826,689 A | 5/1989 | Violanto |
| 4,973,465 A | 11/1990 | Baurain et al. |
| 4,997,454 A | 3/1991 | Violante et al. |
| 5,023,271 A | 6/1991 | Vigne et al. |
| 5,049,322 A | 9/1991 | Devissaguet et al. |
| 5,078,994 A | 1/1992 | Nair et al. |
| 5,091,187 A | 2/1992 | Haynes |
| 5,091,188 A | 2/1992 | Haynes |
| 5,100,591 A | 3/1992 | Leclef et al. |
| 5,118,528 A | 6/1992 | Fessi et al. |
| 5,122,543 A | 6/1992 | Khanna |
| 5,133,908 A | 7/1992 | Stainmesse et al. |
| 5,145,684 A | 9/1992 | Liversidge et al. |
| 5,151,264 A | 9/1992 | Samain et al. |
| 5,152,923 A | 10/1992 | Weder et al. |
| 5,174,930 A | 12/1992 | Stainmesse et al. |
| 5,188,837 A | 2/1993 | Domb |
| 5,246,707 A | 9/1993 | Haynes |
| 5,250,236 A | 10/1993 | Gasco |
| 5,269,979 A | 12/1993 | Fountain |
| 5,298,262 A | 3/1994 | Na et al. |
| 5,302,401 A | 4/1994 | Liversidge et al. |
| 5,314,506 A | 5/1994 | Midler, Jr. et al. |
| 5,318,767 A | 6/1994 | Liversidge |
| 5,326,552 A | 7/1994 | Na et al. |
| 5,336,507 A | 8/1994 | Na et al. |

(Continued)

FOREIGN PATENT DOCUMENTS

| CA | 2029673 | 9/2000 |
|---|---|---|
| EP | 0169618 | 1/1986 |

(Continued)

OTHER PUBLICATIONS

U.S. Pharmacopie monograph USP28: poloxamer.*
Gasco et al., preparation and characterization of solid lipid nanospheres containing paclitaxel, Eur. J. Pharm. Sci., 2000, vol. 10, pp. 305-309.*
Anonymous, Crystal Growing, URL:http://www.chem.tamu.edu/xray/pdf/guide%20to%20crystal%20growth.pdf.
H. von Briesen, "Controled Release of Antiretroviral Drugs", AIDS Rev., 2, pp. 31-38, 2000.
Kinman et al., "Lipid-Drug Association Enhanced IHV-1 Protease Inhibitor Indinavir Localization in Lymphoid Tissues and Viral Load Reduction: A Proof of Concept Study in HIV-$2_{287}$-Infected Macaques", Journal of Acquired Immune Deficiency Syndrome, 34(4), pp.

(Continued)

*Primary Examiner* — Bethany Barham
*Assistant Examiner* — Ping Cao
(74) *Attorney, Agent, or Firm* — Marshall, Gerstein & Borun LLP (57) ABSTRACT

Submicron particles of an organic compound, such as therapeutic and diagnostic agent are disclosed. The organic compound particles are associated with at least two surfactants including a block copolymer and phospholipids conjugated with a hydrophilic polymer.

15 Claims, 8 Drawing Sheets

(56) References Cited

U.S. PATENT DOCUMENTS

| | | |
|---|---|---|
| 5,340,564 A | 8/1994 | Illig et al. |
| 5,346,702 A | 9/1994 | Na et al. |
| 5,352,459 A | 10/1994 | Hollister et al. |
| 5,354,563 A | 10/1994 | Toyotama |
| 5,389,263 A | 2/1995 | Gallagher et al. |
| 5,399,363 A | 3/1995 | Liversidge et al. |
| 5,417,956 A | 5/1995 | Moser |
| 5,429,824 A | 7/1995 | June |
| 5,447,710 A | 9/1995 | Na et al. |
| 5,466,646 A | 11/1995 | Moser |
| 5,470,583 A | 11/1995 | Na et al. |
| 5,474,989 A | 12/1995 | Hashimoto et al. |
| 5,494,683 A | 2/1996 | Liversidge et al. |
| 5,510,118 A | 4/1996 | Bosch et al. |
| 5,518,187 A | 5/1996 | Bruno et al. |
| 5,518,738 A | 5/1996 | Eickhoff et al. |
| 5,534,270 A | 7/1996 | De Castro |
| 5,543,133 A | 8/1996 | Swanson et al. |
| RE35,338 E | 9/1996 | Haynes |
| 5,552,160 A | 9/1996 | Liversidge et al. |
| 5,560,932 A | 10/1996 | Bagchi et al. |
| 5,560,933 A | 10/1996 | Soon-Shiong et al. |
| 5,565,383 A | 10/1996 | Sakai |
| 5,569,448 A | 10/1996 | Wong et al. |
| 5,573,783 A | 11/1996 | Desieno et al. |
| 5,578,325 A | 11/1996 | Domb et al. |
| 5,580,579 A | 12/1996 | Ruddy et al. |
| 5,587,143 A | 12/1996 | Wong |
| 5,591,456 A | 1/1997 | Franson et al. |
| 5,605,785 A | 2/1997 | Texter et al. |
| 5,626,864 A | 5/1997 | Rosenberg et al. |
| 5,635,609 A | 6/1997 | Levy et al. |
| 5,641,515 A | 6/1997 | Ramtoola |
| 5,641,745 A | 6/1997 | Ramtoola |
| 5,660,858 A | 8/1997 | Parikh et al. |
| 5,662,883 A | 9/1997 | Bagchi et al. |
| 5,662,932 A | 9/1997 | Amselem et al. |
| 5,665,331 A | 9/1997 | Bagchi et al. |
| 5,665,383 A | 9/1997 | Grinstaff et al. |
| 5,672,662 A * | 9/1997 | Harris et al. ............... 525/408 |
| 5,707,634 A | 1/1998 | Schmitt |
| 5,716,642 A | 2/1998 | Bagchi et al. |
| 5,720,551 A | 2/1998 | Shechter |
| 5,766,635 A | 6/1998 | Spenleuhauer et al. |
| 5,780,062 A | 7/1998 | Frank et al. |
| 5,833,891 A | 11/1998 | Subramaniam et al. |
| 5,858,410 A | 1/1999 | Muller et al. |
| 5,862,999 A | 1/1999 | Czekai et al. |
| 5,874,111 A | 2/1999 | Maitra et al. |
| 5,885,486 A | 3/1999 | Westesen et al. |
| 5,916,583 A | 6/1999 | Broberg et al. |
| 5,916,596 A | 6/1999 | Desai et al. |
| 5,922,355 A | 7/1999 | Parikh et al. |
| 5,939,100 A | 8/1999 | Albrechtsen et al. |
| 5,968,251 A | 10/1999 | Auweter et al. |
| 5,981,719 A | 11/1999 | Woiszwillo et al. |
| 5,989,583 A | 11/1999 | Amselem |
| 6,007,845 A | 12/1999 | Domb et al. |
| 6,039,981 A | 3/2000 | Woo et al. |
| 6,045,826 A | 4/2000 | Borowy-Borowski et al. |
| 6,045,829 A | 4/2000 | Liversidge et al. |
| 6,048,550 A | 4/2000 | Chan et al. |
| 6,063,138 A | 5/2000 | Hanna et al. |
| 6,063,910 A | 5/2000 | Debenedetti et al. |
| 6,068,858 A | 5/2000 | Liversidge et al. |
| 6,086,376 A | 7/2000 | Moussa et al. |
| 6,090,925 A | 7/2000 | Woiszwillo et al. |
| 6,090,983 A | 7/2000 | Yokoyama et al. |
| 6,132,750 A | 10/2000 | Perrier et al. |
| 6,139,870 A | 10/2000 | Verrecchia |
| 6,143,211 A | 11/2000 | Mathiowitz et al. |
| 6,146,663 A | 11/2000 | Bissery et al. |
| 6,153,225 A | 11/2000 | Lee et al. |
| 6,165,506 A | 12/2000 | Jain et al. |
| 6,177,103 B1 | 1/2001 | Pace et al. |
| 6,197,757 B1 | 3/2001 | Perrier et al. |
| 6,200,598 B1 * | 3/2001 | Needham ............... 424/450 |
| 6,207,134 B1 | 3/2001 | Fahlvik et al. |
| 6,207,178 B1 | 3/2001 | Westesen et al. |
| 6,214,384 B1 | 4/2001 | Pallado et al. |
| 6,217,886 B1 | 4/2001 | Onyuksel et al. |
| 6,221,332 B1 | 4/2001 | Thumm et al. |
| 6,221,398 B1 | 4/2001 | Jakupovic et al. |
| 6,221,400 B1 | 4/2001 | Liversidge et al. |
| 6,228,399 B1 | 5/2001 | Parikh et al. |
| 6,231,890 B1 | 5/2001 | Naito et al. |
| 6,235,224 B1 | 5/2001 | Mathiowitz |
| 6,238,677 B1 | 5/2001 | Fanta et al. |
| 6,238,694 B1 | 5/2001 | Gasco |
| 6,245,349 B1 | 6/2001 | Yiv et al. |
| 6,248,363 B1 | 6/2001 | Patel et al. |
| 6,261,537 B1 | 7/2001 | Klaveness et al. |
| 6,264,922 B1 | 7/2001 | Wood et al. |
| 6,267,989 B1 | 7/2001 | Liversidge |
| 6,268,053 B1 | 7/2001 | Woiszwillo et al. |
| 6,270,806 B1 * | 8/2001 | Liversidge et al. ......... 424/497 |
| 6,294,204 B1 | 9/2001 | Rossling et al. |
| 6,299,906 B1 | 10/2001 | Bausch et al. |
| 6,306,406 B1 | 10/2001 | Deluca |
| 6,337,092 B1 | 1/2002 | Khan et al. |
| 6,344,271 B1 | 2/2002 | Yadav et al. |
| 6,346,533 B1 | 2/2002 | Cha et al. |
| 6,365,191 B1 | 4/2002 | Burman et al. |
| 6,375,986 B1 | 4/2002 | Ryde et al. |
| 6,395,300 B1 | 5/2002 | Straub et al. |
| 6,428,814 B1 | 8/2002 | Bosch et al. |
| 6,458,387 B1 | 10/2002 | Scott et al. |
| 6,462,093 B1 | 10/2002 | Miyamoto et al. |
| 6,607,784 B2 | 8/2003 | Kipp et al. |
| 6,616,869 B2 | 9/2003 | Mathiowitz et al. |
| 6,667,048 B1 | 12/2003 | Lambert et al. |
| 6,682,761 B2 | 1/2004 | Pace et al. |
| 6,703,048 B1 | 3/2004 | Bengs et al. |
| 6,835,396 B2 | 12/2004 | Brynjelsen et al. |
| 6,869,617 B2 | 3/2005 | Kipp et al. |
| 6,884,436 B2 | 4/2005 | Kipp et al. |
| 2001/0007678 A1 | 7/2001 | Baert et al. |
| 2001/0018072 A1 * | 8/2001 | Unger ............... 424/484 |
| 2001/0025058 A1 | 9/2001 | Borowy-Borowski et al. |
| 2001/0042932 A1 | 11/2001 | Mathiowitz et al. |
| 2002/0012675 A1 | 1/2002 | Jain et al. |
| 2002/0041896 A1 | 4/2002 | Straub et al. |
| 2002/0048610 A1 | 4/2002 | Cima et al. |
| 2002/0054912 A1 | 5/2002 | Kim et al. |
| 2002/0110599 A1 | 8/2002 | Auweter et al. |
| 2002/0168402 A1 | 11/2002 | Kipp et al. |
| 2003/0003155 A1 | 1/2003 | Kipp et al. |
| 2003/0044433 A1 | 3/2003 | Werling et al. |
| 2003/0072807 A1 | 4/2003 | Wong et al. |
| 2003/0077329 A1 | 4/2003 | Kipp et al. |
| 2003/0096013 A1 | 5/2003 | Werling et al. |
| 2003/0100568 A1 | 5/2003 | Werling et al. |
| 2003/0170279 A1 | 9/2003 | Lambert et al. |
| 2003/0206959 A9 | 11/2003 | Kipp et al. |
| 2003/0211083 A1 | 11/2003 | Vogel et al. |
| 2004/0022861 A1 | 2/2004 | Williams |
| 2004/0022862 A1 | 2/2004 | Kipp et al. |
| 2004/0043077 A1 | 3/2004 | Brown |
| 2004/0245662 A1 | 12/2004 | Chaubal |
| 2004/0256749 A1 | 12/2004 | Chaubal |
| 2005/0013868 A1 | 1/2005 | Brynjelsen et al. |
| 2005/0037083 A1 | 2/2005 | Brynjelsen et al. |
| 2005/0048126 A1 | 3/2005 | Rabinow et al. |
| 2005/0170002 A1 | 8/2005 | Kipp et al. |
| 2006/0134150 A1 | 6/2006 | Werling et al. |
| 2006/0222710 A1 | 10/2006 | Kipp et al. |
| 2006/0222711 A1 | 10/2006 | Kipp et al. |

FOREIGN PATENT DOCUMENTS

| | | |
|---|---|---|
| EP | 0207134 | 1/1987 |
| EP | 0275796 | 7/1988 |
| EP | 0349428 | 1/1990 |
| EP | 0372070 | 6/1990 |

(56) References Cited

FOREIGN PATENT DOCUMENTS

| | | |
|---|---|---|
| EP | 0377477 | 7/1990 |
| EP | 0379379 | 7/1990 |
| EP | 0498482 | 8/1992 |
| EP | 0499299 | 8/1992 |
| EP | 0517565 | 12/1992 |
| EP | 0535534 | 4/1993 |
| EP | 0577215 | 1/1994 |
| EP | 0600532 | 6/1994 |
| EP | 0601618 | 6/1994 |
| EP | 0601619 | 6/1994 |
| EP | 0602700 | 6/1994 |
| EP | 0602702 | 6/1994 |
| EP | 0605024 | 7/1994 |
| EP | 0644755 | 3/1995 |
| EP | 0720471 | 7/1996 |
| EP | 0730406 | 9/1996 |
| EP | 0752245 | 1/1997 |
| EP | 0754034 | 1/1997 |
| EP | 0788350 | 8/1997 |
| EP | 0804162 | 11/1997 |
| EP | 0808154 | 11/1997 |
| EP | 0812187 | 12/1997 |
| EP | 0820300 | 1/1998 |
| EP | 0828479 | 3/1998 |
| EP | 0831770 | 4/1998 |
| EP | 0832569 | 4/1998 |
| EP | 1023050 | 1/1999 |
| EP | 0988863 | 3/2000 |
| EP | 1012204 | 6/2000 |
| EP | 1105109 | 6/2001 |
| EP | 1156788 | 11/2001 |
| EP | 1210942 | 6/2002 |
| EP | 1347747 | 10/2003 |
| FR | 2817478 | 6/2002 |
| JP | 02306902 | 12/1990 |
| WO | WO-85/00011 | 1/1985 |
| WO | WO-86/03676 | 7/1986 |
| WO | WO-89/11850 | 12/1989 |
| WO | WO-90/03782 | 4/1990 |
| WO | WO-90/15593 | 12/1990 |
| WO | WO-91/06292 | 5/1991 |
| WO | WO-91/07170 | 5/1991 |
| WO | WO-91/12794 | 9/1991 |
| WO | WO-91/16068 | 10/1991 |
| WO | WO-92/00731 | 1/1992 |
| WO | WO-92/03380 | 3/1992 |
| WO | WO-93/25190 | 12/1993 |
| WO | WO-94/20072 | 9/1994 |
| WO | WO-95/05164 | 2/1995 |
| WO | WO-95/27482 | 10/1995 |
| WO | WO-95/33488 | 12/1995 |
| WO | WO-96/00567 | 1/1996 |
| WO | WO-96/14833 | 5/1996 |
| WO | WO-96/20698 | 7/1996 |
| WO | WO-96/24336 | 8/1996 |
| WO | WO-96/24340 | 8/1996 |
| WO | WO-96/25150 | 8/1996 |
| WO | WO-96/25152 | 8/1996 |
| WO | WO-96/25918 | 8/1996 |
| WO | WO-96/31231 | 10/1996 |
| WO | WO 97/03651 A1 | 2/1997 |
| WO | WO-97/03657 | 2/1997 |
| WO | WO-97/14407 | 4/1997 |
| WO | WO-97/30695 | 8/1997 |
| WO | WO-97/36611 | 10/1997 |
| WO | WO-97/41837 | 11/1997 |
| WO | WO-97/44014 | 11/1997 |
| WO | WO-98/07410 | 2/1998 |
| WO | WO-98/07414 | 2/1998 |
| WO | WO-98/14174 | 4/1998 |
| WO | WO-98/14180 | 4/1998 |
| WO | WO 98/24450 A1 | 6/1998 |
| WO | WO-98/35666 | 8/1998 |
| WO | WO 98/47492 A1 | 10/1998 |
| WO | WO 98/56362 | 12/1998 |
| WO | WO-98/57967 | 12/1998 |
| WO | WO 99/00113 A1 | 1/1999 |
| WO | WO-99/02665 | 1/1999 |
| WO | WO-99/03450 | 1/1999 |
| WO | WO-99/16443 | 4/1999 |
| WO | WO-99/29316 | 6/1999 |
| WO | WO-99/30833 | 6/1999 |
| WO | WO-99/32156 | 7/1999 |
| WO | WO-99/33467 | 7/1999 |
| WO | WO-99/38493 | 8/1999 |
| WO | WO 99/39700 A1 | 8/1999 |
| WO | WO-99/49846 | 10/1999 |
| WO | WO-99/49848 | 10/1999 |
| WO | WO-99/59550 | 11/1999 |
| WO | WO-99/61001 | 12/1999 |
| WO | WO-99/65469 | 12/1999 |
| WO | WO-00/03697 | 1/2000 |
| WO | WO 00/06152 A1 | 2/2000 |
| WO | WO-00/09096 | 2/2000 |
| WO | WO-00/12124 | 3/2000 |
| WO | WO-00/12125 | 3/2000 |
| WO | WO-00/18374 | 4/2000 |
| WO | WO-00/27363 | 5/2000 |
| WO | WO-00/30615 | 6/2000 |
| WO | WO-00/30616 | 6/2000 |
| WO | WO-00/37050 | 6/2000 |
| WO | WO-00/40220 | 7/2000 |
| WO | WO-00/51572 | 9/2000 |
| WO | WO-00/56726 | 9/2000 |
| WO | WO-00/71079 | 11/2000 |
| WO | WO-01/12155 | 2/2001 |
| WO | WO-01/17546 | 3/2001 |
| WO | WO-01/21154 | 3/2001 |
| WO | WO-01/26635 | 4/2001 |
| WO | WO-01/62374 | 8/2001 |
| WO | WO-01/64164 | 9/2001 |
| WO | WO-01/80828 | 11/2001 |
| WO | WO-01/85345 | 11/2001 |
| WO | WO-01/87264 | 11/2001 |
| WO | WO-02/17883 | 3/2002 |
| WO | WO-02/24163 | 3/2002 |
| WO | WO-02/24169 | 3/2002 |
| WO | WO-02/43702 | 6/2002 |
| WO | WO-02/051386 | 7/2002 |
| WO | WO 02/055059 A2 | 7/2002 |
| WO | WO-02/060411 | 8/2002 |
| WO | WO-02/072070 | 9/2002 |
| WO | WO-02/072071 | 9/2002 |
| WO | WO-02/074282 | 9/2002 |
| WO | WO-02/080678 | 10/2002 |
| WO | WO-02/080883 | 10/2002 |
| WO | WO-02/089773 | 11/2002 |
| WO | WO-03/026611 | 4/2003 |
| WO | WO-03/035031 | 5/2003 |
| WO | WO-03/045330 | 6/2003 |
| WO | WO-2004/082659 | 9/2004 |
| WO | WO-2004/103348 | 12/2004 |

OTHER PUBLICATIONS

Moghimi et al., "Long-Circulating and Target-Specific Nanoparticles: Theory to Practice", Pharmacological Reviews, 53, pp. 283-318, 2001.

Shrayer, et al., "Ceramide, a mediator of apoptosis, synergizes with paclitaxel to induce regression of the L 3.6 human pancreatic carcinoma implanted in SCDI mice", Journal of Clinical Oncology, vol. 22, No. 14S, Abstract, 2004:2135.

Allen et al., "Effects on the murine mononuclear phagocyte system of chronic administration of liposomes containing drug or lipid A compared with empty liposomes", Can. J. Physiol. Pharmacol., vol. 65, pp. 185-190. 1987.

Heiati, H., et al. "Solid Lipid Nanoparticles as Drug Carriers II. Plasma Stability and Biodistribution of Solid Lipid Nanoparticles Containing the Lipophilic Prodrug 3'-azido-3'-deoxythymidine almitate in Mice", Int'l Journal of Pharmaceutics, 174, pp. 71-80, 1998.

Allen et al., "Critical evaluation of acute cardiopulmonary toxicity of microspheres," J. Nucl. Med., 19:1204-1208 (1987).

(56) References Cited

OTHER PUBLICATIONS

Avanti Polar Lipids, Inc., "Polymer and polymerizable lipids: functionalized PEG lipids," (Mar. 2003). Retrieved from the Internet : <URL: http://www.avantilipids.com>.

Avant Polar Lipids, Inc., "Polymer and polymerizable lipids: polyethylene glycol)-lipid conjugates," (Mar. 2003). Retrieved from the Internet: <URL: http://www.avantilipids.com>.

Avanti Polar Lipids, Inc., "Synthetic products—functionalized phospholipids: lipids for conjugation of proteins/pepetides/drugs to lipsomes," (Mar. 2003). Retrieved from the Internet: <URL: http://www.avantilipids.com>.

Davis et al., "Pulmonary perfusion imaging: acute toxicity and safety factors as a function of particle size," *J. Nucl. Med.*, 19:1209-1213 (1978).

Duncker et al., "Effects of the pharmaceutical cosolvent hydroxypropyl-beta-cyclodextrin on porcine corneal endothelium," *Graefes Arch. Clin. Exp. Opthalmol.*, 236::380-389 (1998).

Schroeder et al., "Physiological effects of subvisible microspheres administered intravenously to beagle dogs," *J. Pharm. Sci.*, 67:508-513 (1978).

Singla et al., "Paclitaxel and its formulations," *Int. J. Pharm.*, 235:179-192 (2002).

Sjostrom et al., "A method for the preparation of submicron particles of sparingly water-soluble drugs by precipitation in oil-in-water emulsions. II: Influence of the emulsifier, the solvent, and the drug substance," *J. Pharm. Sci.*, 82:584-589 (1993).

Sjostrom et al., "Preparation of submicron drug particles in lecithin-stabilized o/w emulsions I. Model studies of the precipitation of cholesteryl acetate," *Int. J. Pharm.*, 88:53-62 (1992).

Sjostrom et al., "The formation of submicron organic particles by precipitation in an emulsion," *J. Dispers. Sci. Tech.*, 15:89-117 (1994).

Volcheck et al., "Anaphylaxis to intravenous cyclosporine and tolerance to oral cyclosporine: case report and review," *Ann. Allergy Asthma Immunol.*, 80:159-163 (1998).

Yokel et al., "Acute toxicity of latex microspheres," *Toxicol. Lett.*, 9:165-170 (1981).

Eugen Muller (ed.), *Methoden der Organischen Chemie-Allgemeine Laboratoriumspraxis*, p. 375, Stuttgart, Germany: Georg Thieme Verlag (1958).

European Search Report and Opinion in counterpart European Application No. 05077486.8, dated Mar. 7, 2007.

European Search Report (corrected) in counterpart European Application No. 05077486.8, dated May 11, 2007.

Chen et al., In vitro and in vivo study of two types of long-circulating solid lipid nanoparticles containing paclitaxel, Chem. Pharm. Bull., 49(11):1444-7 (2001).

Allen et al., Large unilamellar liposomes with low uptake into the reticuloendothelial system, FEBS letters, 1987, vol. 223, pp. 42-46.

\* cited by examiner

FIG. 1: Method A

FIG. 2: Method B

FIG. 3: Dissolution of two formulations of submicron paclitaxel

FIG. 4: Effect of various stressed conditions on the particle size of submicron particles of paclitaxel FIG. 5: Effect of storage on the particle size of submicron particles of paclitaxel

FIG. 6

FIG. 7: Effect of stress on particle size

FIG. 8: Effect of storage on particle size

SURFACTANT SYSTEMS FOR DELIVERY OF ORGANIC COMPOUNDS

CROSS-REFERENCE TO RELATED APPLICATIONS

This application is a continuation-in-part of application Ser. No. 10/703,395, filed on Nov. 7, 2003 now U.S. Pat. No. 8,067,032 which is a continuation-in-part of application Ser. No. 10/390,333 filed on Mar. 17, 2003, now abandoned which is a continuation-in-part of application Ser. No. 10/246,802 filed on Sep. 17, 2002, now abandoned which is a continuation-in-part of application Ser. No. 10/035,821 filed on Oct. 19, 2001, now U.S. Pat. No. 6,977,085 which is a continuation-in-part of application Ser. No. 09/953,979 filed Sep. 17, 2001 now U.S. Pat. No. 6,951,656 which is a continuation-in-part of application Ser. No. 09/874,637 filed on Jun. 5, 2001, now U.S. Pat. No. 6,969,617 which claims priority from provisional application Ser. No. 60/258,160 filed Dec. 22, 2000. All of the above-referenced applications are incorporated herein by reference and made a part hereof.

FEDERALLY SPONSORED RESEARCH OR DEVELOPMENT

Not Applicable.

BACKGROUND OF THE INVENTION

Technical Field

The present invention relates to systems and methods for the delivery of insoluble or poorly soluble organic compound, such as therapeutic, and/or diagnostic agents. More particularly, the present invention relates to surfactants and surfactant systems used with such compounds.

Background Art

Many organic compounds that are useful in therapeutic or diagnostic applications are poorly soluble or insoluble in aqueous environments. Because of their poor solubility such compounds present challenges to delivering them by traditional administrative routes. Recently, efforts have been made to develop methods and systems whereby such non-soluble and poorly soluble compounds can be delivered to a patient. These efforts have led to the development of different types of drug delivery vehicles.

One approach for delivering poorly soluble or insoluble compounds is to formulate the compound as a solid particle suspension. Compounds that are insoluble in water can be formulated as a stable suspension of sub-micron sized particles in an aqueous medium such as microparticulate or nanoparticulate suspensions. In this way, compounds that were previously unable to be formulated in an aqueous based system can be made suitable for intravenous administration.

Solid particle suspensions of nanoparticles are commonly referred to as nanosuspensions. Nanoparticles range in particle size from about 10 nm to about 10 microns, preferably from about 100 nm to about 2 microns and, more preferably, from about 400 nm to about 1,000 nm. Nanoparticles also are generally coated with or have associated on their surfaces one or more surfactants or other excipients in order to prevent agglomeration, flocculation or what are referred to as Ostwald ripening of the nanoparticles.

Sub-micron sized particles generally and nanoparticles specifically may be administered parenterally. In addition, preparations of small particles of water insoluble compounds may also be suitable for oral, pulmonary, topical, ophthalmic, nasal, buccal, rectal, vaginal, transdermal, or other routes of administration. The small size of the particles improves the dissolution rate of the compound, and hence improves its bioavailability and potentially its toxicity profiles. The particle size will depend on the route of administration, formulation, solubility, and bioavailability of the compound. For example, for oral administration, it is desirable to have a particle size of less than about 7 microns. For pulmonary administration, the particles are preferably less than about 10 microns in size.

One approach for preparing a nanosuspension is described in U.S. Pat. No. 6,607,784, assigned to the assignee of the present application and incorporated herein by reference and made a part hereof. The '784 patent discloses a method for preparing submicron sized particles of an organic compound, wherein the solubility of the organic compound is greater in a water-miscible selected solvent than in another solvent which is aqueous. The process described in the '784 patent generally includes the steps of (i) dissolving the organic compound in the water-miscible selected solvent to form a first solution, (ii) mixing the first solution with a second solvent to precipitate the compound to define a pre-suspension; and (iii) adding energy to the pre-suspension to form particles which can be of submicron size. Often, the average effective particle size can range between about 400 nm to 1,000 nm or below, extending into low micron size, typically no greater than about 2 microns.

Other examples of insoluble compound delivery systems and methods are disclosed in U.S. Pat. Nos. 5,858,410 and 5,922,355. The '355 patent discloses providing submicron sized particles of insoluble compounds using a combination of surface modifiers and a phospholipid, followed by particle size reduction using techniques such as sonication, homogenization, milling, microfluidization, precipitation or recrystallization.

Another approach for providing formulations of insoluble compounds for parenteral delivery is disclosed in U.S. Pat. No. 5,145,684. The '684 patent discloses the wet milling of an insoluble drug in the presence of a surface modifier to provide a particle having an average effective particle size of less than 400 nm. The surface modifier is adsorbed on the surface of the particle in an amount sufficient to prevent agglomeration into larger particles.

In addition to nanoparticulates and nanosuspensions discussed above, other vehicles for delivering insoluble or poorly soluble compounds have also been considered. These include micelles, liposomes, microemulsions, emulsions, nanocapsules, and other dispersed phase (including nanodispersed phase) systems.

Micelles have been considered as vehicles for delivering pharmaceutical components. Micelles are typically spherical structures comprised of a conglomeration of surfactant molecules, formed as a result of the interaction between the hydrophobic parts of the surfactant molecules.

Liposomes have also been considered as vehicles for delivering pharmaceutical components. Liposomes are comprised of a conglomeration of surfactant molecules having one or several bi-layer structures, normally comprising lipid with an aqueous cavity therein. Liposomes possess the capability to incorporate both water-soluble and oil-soluble substances.

Organic compounds such as therapeutic or diagnostic agents may also be delivered in a microemulsion or an emulsion. Microemulsions are bicontinuous structures having only a monolayer wall, comprised generally of water, oil and surfactant(s), (which constitute a single optically isotropic and thermodynamically stable liquid solution.) The size of microemulsion droplets ranges from about 10-100 nm. Microemulsions have the capacity to solubilize both water-soluble and oil-soluble compounds. Accordingly, for delivery, microemulsions can be comprised of oil droplets in an aqueous continuum, water in an oil continuum, or a bicontinuous structures. Other suitable vehicles include cubosomes, which are dispersions of one of the bicontinuous cubic phases that have a lamellar wall, and hexasomes which are dispersions of hexagonal phases that have a lamellar wall.

As noted above, other vehicles for delivering organic compounds such as therapeutic or diagnostic agents are emulsions. Emulsions comprise droplets which are relatively large in size (as compared to microemulsions.) In contrast to microemulsions which form spontaneously, emulsions must be prepared with the input of energy. Formation of emulsions includes high pressure homogenization for producing emulsion droplets (ranging in size from about 100 nm-10 μm) and generating a new surface thereon. Emulsions may be water-in-oil or oil-in-water based on surfactants, oil and water volume fraction, temperature, salt concentration, and the presence of co-surfactants and other co-solutes.

One challenge in the area of insoluble organic compound delivery is that many of the poorly soluble or insoluble compounds, when formulated into submicron sized particles such as nanoparticles, and the like, exhibit undesirable particle growth and/or aggregation (e.g., agglomeration), due in part to the surface activity of the compound. Accordingly, the particle, (emulsion or suspension) may include a selected amount of one or more surfactants that protect the particle form such growth and aggregation, and generally stabilize the particle or other composition and the active ingredient therein.

Surfactants are generally low to moderate weight compounds which contain a hydrophobic portion, which is generally readily soluble in oil, but sparingly soluble or insoluble in water, and a hydrophilic portion, which is sparingly soluble or insoluble in oil, but readily soluble in water. In addition to protecting against growth and aggregation and stabilizing the organic compound delivery vehicle, surfactants are also useful as excipients in organic compound delivery systems and formulations because they increase the effective solubility of an otherwise poorly soluble or non-soluble organic compound, and may decrease hydrolytic degradation, decrease toxicity and generally improve bioavailability. They may also provide selected and advantageous effects on drug release rate and selectivity of drug uptake. Surfactants are generally classified as either anionic, cationic, or nonionic.

Some surfactants suffer from poor physiological compatibility upon injection and/or do not provide effective long term stability. In addition, sub-micron sized particles and other organic compound delivery vehicles that are injected intravenously are often recognized and scavenged by the reticoendothelial system (RES) of the liver, thereby preventing the nanoparticles from being delivered to the target organs.

Thus, it would be desirable to provide a surfactant or combination of surfactants that are effective stabilizers of the submicron sized particles or other organic compound delivery vehicle or system, are safe and physiologically compatible, and protect the particle or other vehicle from being scavenged by the RES of the liver.

SUMMARY OF THE INVENTION

In one aspect, the present invention is directed to a composition including an organic compound and at least two surfactants associated therewith. The surfactants include a block copolymer of polyoxyethylene and polyoxypropylene combined with an amphiphilic compound conjugated with a hydrophilic polymer.

In another aspect, the present invention is directed to a composition including an organic compound and at least two surfactants associated therewith. Relative to each other, the at least two surfactants include approximately 90-10% (w/v) of the block copolymer $HO(CH_2CH_2O)_{80}(CH_3H_6O)_{27}(CH_2CH_2O)_{80}H$ and approximately 10-90% (w/w) of an amphiphilic compound conjugated with a hydrophilic polymer.

In another aspect, the present invention is directed to a composition including an organic compound and at least two surfactants associated therewith. Relative to each other, the at least two surfactants include approximately 90-10% (w/w) of a block copolymer of polyethylene and polyoxypropylene and approximately 10-90% (w/w) of a peglyated phosphatidyl ethanolamine.

In another aspect, the present invention is directed to a method for making submicron particles of an organic compound, the particles having a mean particle size of about 10 nm to about 10 μm. The method includes dissolving the compound in a water miscible solvent to form a first solution and preparing an aqueous solution including at least two surfactants. Relative to each other, the at least two surfactants include approximately 90-10% (w/w) of a block copolymer of polyoxyethylene and polyoxypropylene and approximately 10-90% (w/w) of an amphiphilic compound conjugated with a hydrophilic polymer. The method further includes adding the first solution to the aqueous solution to form a presuspension, and adding energy to the presuspension.

In still another aspect, the present invention is directed to a method for making particles of an organic compound, the particles having a mean particle size of about 10 nm to about 10 μm. The method includes adding an organic compound and at least two surfactants wherein, relative to each other, the at least two surfactants 90-10% (w/w) of a block copolymer of polyoxyethylene and polyoxypropylene and 10-90% (w/w) of a hydrophilic polymer conjugated with a phospholipid to a milling apparatus and forming a mixture. A suitable grinding media is also added to the milling apparatus. The method further includes milling the mixture in the presence of the grinding media.

In a further aspect, the present invention is directed to a method of administering an effective amount of a composition comprising particles including an organic compound associated with at least two surfactants to a subject. The particles have a mean particle size of about 10 nm to about 10 μm. Relative to each other, the at least two surfactants include 90-10% (w/w) of a block copolymer of polyoxyethylene and polyoxypropylene and 10-90% (w/w) of an amphiphilic compound conjugated with a hydrophilic compound.

These and other aspects and attributes of the present invention will be discussed with reference to the following drawings and accompanying specification.

DETAILED DESCRIPTION OF THE INVENTION

The present invention may be embodied in many different forms. Preferred embodiments of the invention are disclosed with the understanding that the present disclosure is to be considered as an exemplification of the principles of the invention and are not intended to limit the broad aspects of the invention to the embodiments illustrated.

The present invention provides compositions of non-soluble or poorly soluble organic compounds intended for delivery to a patient or human subject, typically for therapeutic or diagnostic purposes. An organic compound for use in the process of this invention is any organic chemical entity whose solubility decreases from one solvent to another. This organic compound might be a pharmaceutically active compound, which can be selected from therapeutic agents, diagnostic agents, cosmetics, nutritional supplements, and pesticides. Examples of such agents and compounds are provided in U.S. patent application Ser. No. 10/703,395, filed Nov. 7, 2003, published as U.S. Publication No. 2004/0245662 A1, from which the present application claims priority and which is incorporated by reference in its entirety. In addition to therapeutic agents, diagnostic agents, such as x-ray imaging agents and contrast media can be prepared as submicron particles.

A description of classes of therapeutic agents and diagnostic agents and a listing of species within each class can also be found in Martindale, The Extra Pharmacopoeia, Twenty-ninth Edition, The Pharmaceutical Press, London, 1989 which is incorporated herein by reference and made a part hereof. The therapeutic agents and diagnostic agents are commercially available and/or can be prepared by techniques known in the art.

The agent or other organic compound is at least poorly water-soluble. What is meant by "poorly water soluble" is a solubility of the compound in water of less than about 10 mg/mL, and preferably less than 1 mg/mL. These poorly water-soluble agents are most suitable for aqueous suspension preparations since there are limited alternatives of formulating these agents in an aqueous medium.

In accordance with one preferred embodiment, the vehicle for delivering the compound may be in particulate form. Preferably, such particles have a mean particle size of generally less than about 100 μm as measured by dynamic light scattering methods, e.g., photocorrelation spectroscopy, laser diffraction, low-angle laser light scattering (LALLS), medium-angle laser light scattering (MALLS), light obscuration methods (Coulter method, for example), rheology, or microscopy (light or electron). However, the particles can be prepared in a wide range of sizes, such as from about 20 μm to about 10 nm, from about 10 μm to about 10 nm, less than 2 μm and more particularly from about 2 μm to about 10 nm, from about 1 μm to about 10 nm, from about 400 nm to about 50 nm, from about 200 nm to about 50 nm or any range or combination of ranges therein. The preferred mean particle size depends on factors such as the intended route of administration, formulation, solubility, toxicity and bioavailability of the compound.

To be suitable for parenteral administration, the particles preferably have a mean particle size of less than about 7 μm, and more preferably less than about 2 μm or any range or combination of ranges therein. Parenteral administration includes intravenous, intra-arterial, intrathecal, intraperitoneal, intraocular, intra-articular, intradural, intraventricular, intrapericardial, intramuscular, intradermal or subcutaneous injection.

Particles sizes for oral dosage forms can be in excess of 2 μm. The particles can range in size up to about 100 μm, provided that the particles have sufficient bioavailability and other characteristics of an oral dosage form. Oral dosage forms include tablets, capsules, caplets, soft and hard gel capsules, or other delivery vehicle for delivering a drug by oral administration.

The present invention is further suitable for providing particles of the organic compound in a form suitable for pulmonary administration. Particles sizes for pulmonary dosage forms can be in excess of 500 nm and typically less than about 10 μm. The particles in the suspension can be aerosolized and administered by a nebulizer for pulmonary administration. Alternatively, the particles can be administered as dry powder by a dry powder inhaler after removing the liquid phase from the suspension, or the dry powder can be resuspended in a non-aqueous propellant for administration by a metered dose inhaler. An example of a suitable propellant is a hydrofluorocarbon (HFC) such as HFC-134a (1,1,1,2-tetrafluoroethane) and HFC-227ea (1,1,1,2,3,3,3-heptafluoropropane). Unlike chlorofluorcarbons (CFC's), HFC's exhibit little or no ozone depletion potential.

Dosage forms for other routes of delivery, such as nasal, topical, ophthalmic, nasal, buccal, rectal, vaginal, transdermal and the like can also be formulated from the particles made from the present invention.

Although a detailed description of the methods for making submicron-sized particles or other organic compound delivery vehicles (such as emulsions, microemulsions, liposomes, micelles etc.) is beyond the scope of the present invention, a brief description of a preferred method of making one preferred category of vehicle, namely, submicron-sized particles, such as nanoparticles, is provided below.

Figure 1:
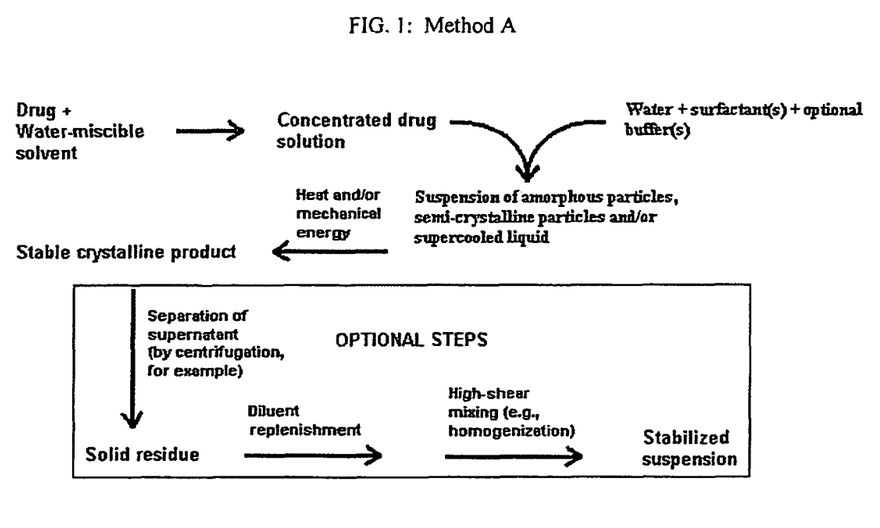
FIG. 1 is a diagrammatic representation of one method of making nanoparticles.

As shown in FIG. 1, (referred to Method A) the organic compound is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent. One example of suitable solvent is N-methyl-2-pyrolidinone (NMP).

As set forth above, the organic compound delivery vehicles such as nanoparticles are typically combined with surfactants selected to prevent agglomeration, stabilize the compound and, preferably, act as an excipient for the compound. Thus, a second aqueous solvent is provided with one or more optional surface modifiers such as an anionic surfactant, a cationic surfactant, a nonionic surfactant or a biologically surface active molecule added thereto. U.S. patent application Ser. No. 10/703,395 (from which priority is claimed) describes suitable anionic, cationic and non-ionic surfactants.

The first solution is then mixed or otherwise combined with the second aqueous solvent to define a pre-suspension of particles. Further steps include adding energy to the pre-suspension to form a suspension of submicron-sized particles. Additional details and alternative steps to this method of making submicron-sized particles are provided in U.S. Pat. No. 6,607,784, previously incorporated by reference, and will not be repeated here.

Figure 2:
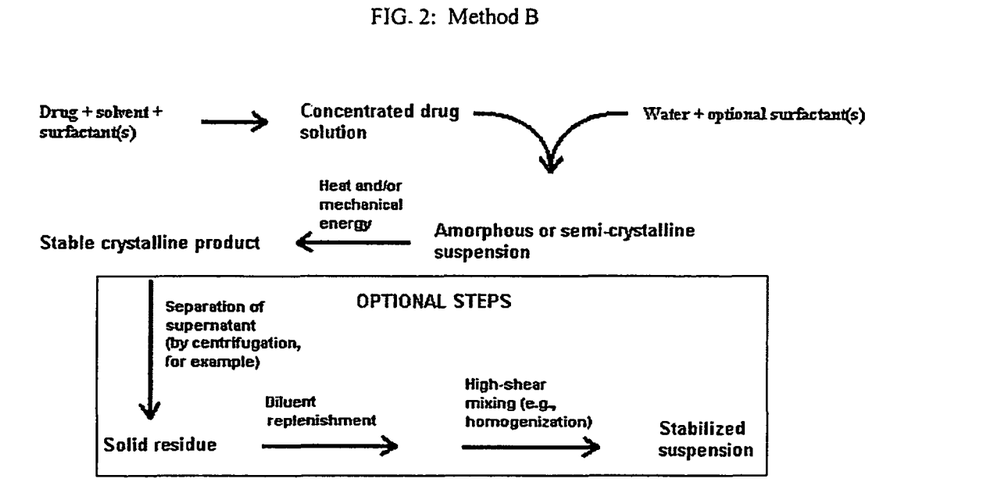
FIG. 2 is a diagrammatic representation of another method of making nanoparticles.

(In an alternative method of manufacturing sub-micron sized particles, the surfactant or combination of surfactants are initially combined with the first solution containing the organic compound. This method is shown in FIG. 2 and referred to as Method B. In all other respects, the method is identical to Method A shown in FIG. 1).

Sub-micron sized particles with the surfactant system of the present invention may also be made by combining the organic compound, the block copolymer and the conjugated amphiphilic to form a mixture, adding a suitable grinding media to the mixture, and milling the mixture in the presence of the grinding media, as generally disclosed in U.S. Pat. No. 5,145,684, incorporated herein by reference.

Surfactant systems of the present invention include an amphiphilic surfactant such as a phospholipid or a ceramide. The phospholipids may be either synthetic or natural semi-synthetic, salted or desalted, hydrogenated or partially hydrogenated. Phospholipids useful in the present invention may include fatty chains of at least 10 carbon atoms with varying degrees of saturation. The phospholipids may be diacyl phospholipids including dimyristoyl (14:0), dipalmitoyl (16:0), distearoyl (18:0), dioleolyl (18:1), or heterogeneous diacyl phospholipids, such as palmitoylstearoyl and the like. For example, the phospholipid may be a diacyl-glycero-phosphethanolamine such as: dimyristoyl-glycero-phosphoethanolamine (DMPE), dipalmitoyl-glycero-hosphoethanolamine (DPPE), distearoyl-glycero-phosphoethanolamine (DSPE), dioleolyl-glycero-phosphoethanolamine (DOPE) or the like. Other suitable phospholipids types include phosphatidylcholines, other phosphatidylethanolamines, phosphatidylserines, phosphatidylinositols, phosphatidylglycerols, phosphatidic acids, lysophospholipids, egg or soybean phospholipids or a combination thereof. As discussed below, the phospholipids or ceramides are preferably conjugated with a water-soluble or hydrophilic polymer.

In one embodiment, the water-soluble or hydrophilic polymer conjugating to the phospholipids (or ceramide) may be polyethylene glycol (PEG). The molecular weight of the PEG may preferably be at least 200 to about 100,000 and more preferably, between about 200-50,000. Examples of suitable PEGs include, but are not limited to, PEG 350, PEG 550, PEG 750, PEG 1000, PEG 2000, PEG 3000, and PEG 5000. The PEGs may be simple PEGs, containing the repeating oxyethylene monomer, or further derivatized. A preferred PEG of the present invention is "mPEG," which is a methoxylated PEG. Conjugated lipids, of the type described above, are available from Avanti Polar Lipids, Inc. of Alabaster, Ala. Other hydrophilic polymer conjugates can also be used, e.g., dextran, hydroxypropyl methacrylate (HPMA), polyglutamate and the like, although PEG is preferred.

Thus, in a preferred embodiment, the surfactant combination includes a polyethylene glycol (PEG) i.e., "peglyated"-lipid conjugate. The conjugated PEG-lipids may be a PEG conjugated to phosphatidyl-ethanoalamine having the structure:

where: $R_1$=alkyl, alkenyl
$R_2$=alkyl, alkenyl

Alternatively, the PEG moiety may be linked to ceramide, and having the structure:

where: $R_1$=alkyl, alkenyl
$R_2$=alkyl, alkenyl

In accordance with the present invention, the conjugated amphiphile is combined with a second surface modifier to further stabilize the particles. The second surface modifier can be mixed into the water-miscible first solvent or the second solvent or both the water-miscible first solvent and the second solvent. The second surface modifier can be selected from anionic surfactants, cationic surfactants, non-ionic surfactants and surface active biological modifiers as described in detail previously in this application.

A preferred second surface modifier is a nonionic surfactant that is a block copolymer of polyoxyethylene and polyoxypropylene or "poloxamer". Poloxamers come in a variety of types and are sometimes referred to and are sold under the trade name PLURONIC® from BASF Aktiengesellschaft. Examples of suitable poloxamers are Poloxamer 188 (Pluronic F-68), Poloxamer 124, Poloxamer 237, Poloxamer 338 and Poloxamer 407. Of these, Poloxamer 188 is most preferred.

A particularly preferred surfactant system for nanoparticles of different therapeutic, diagnostic agents or other organic compounds is one that combines the above-described Poloxamer 188 with the conjugated hydrophilic polymer/phospholipid mPEG-DSPE(2000). As previously described, Poloxamer 188 is a polyoxyethylene-polyoxypropylene copolymer that is a non-ionic surfactant with good physiological compatibility. Poloxamer 188 has the following chemical formula:

$HO(CH_2CH_2O)_{80}(CH_3H_6O)_{27}(CH_2CH_2O)_{80}H$

The phospholipid is a phosphatidyl ethanolamine of which a preferred example is DSPE such as 1,2-Distearoyl-sn-glycero-3-phosphoethanolamine. The DSPE is preferably conjugated with the hydrophilic polymer polyethylene glycol moiety mPEG(2000)[methoxy(polyethyleneglycol)-2000]. The resulting polymer-phospholipid conjugate is 1,2-Distearoyl-sn-glycero-3-phosphoethanolamine N-[methoxy(polyethyleneglycol)-2000], or mPEG-DSPE (2000).

The concentrations of surfactants employed in the composition will depend on the particular organic compound employed in the composition and its concentration, but will be in an amount sufficient to avoid substantial aggregation of the particles and effectively stabilize the system. In general, with higher concentrations of organic compound employed, typically higher concentrations of surfactants will also be employed. It is believed, however, that the surfactants will be employed in compositions that have organic compound concentrations of up to 50% (w/v), but more preferably about 0.05-20% (w/v) where the composition is provided as a "ready-to-use" liquid or as a frozen liquid. Thus, for the preferred organic compound concentration range (e.g., 0.05-20% w/v), the surfactants will be present in concentrations from about 0.01 to about 10% (w/v) of the composition and more preferably, from about 0.1-1.0% (w/v) of the composition. (The remainder of the composition will typically include water, salts and toxicity adjusters.)

The composition of the present invention may also be provided as a solid, including, but not limited to freeze-dried or lyophilized forms. When provided as a solid, the weight ratio of the organic compound to surfactant will typically be from about 1:1 to 20:1, with a weight ratio of 5:1 organic compound to the combined surfactant being preferred.

Regardless of the form in which the composition is provided (i.e., liquid "ready-to-use," frozen liquid, lyophilized or other solid form), relative to each other, the two surfactants will be present in an amount of about 10%-90% (w/w) of the conjugated conjugated amphiphile and 90-10% (w/w) of the block copolymer, relative to total weight of surfactant. More preferably, surfactant systems of the present invention include approximately 20%-40% (w/w) of the conjugated amphiphile and approximately 60%-80% (w/w) of the block copolymer, relative to total surfactant weight. In general, it is preferred that the ratio of block copolymer (e.g., Poloxamer) to conjugated lipid (e.g., MPEG-DSPE) be greater than 1:1, although an approximately 50/50% (w/w) mixture of the two surfactants, relative to total surfactant weight have also been shown to be effective.

The surfactant system described above is safe and biocompatible and provides good stability (and longer shelf life) for submicron sized particles. More particularly, in nanoparticles coated with this surfactant system, agglomeration of nanoparticles is substantially reduced. In addition, this system substantially prevents ripening of the nanoparticles (i.e., the dissolution and subsequent crystallization of smaller particles onto larger particles). Finally, nanoparticles coated with the surfactant system are less susceptible to scavenging by the reticuloendothelial system (RES) of the liver, a problem that is observed with other surfactant compounds. Avoiding scavenging by the RES allows the nanoparticle and, thus, the therapeutic or diagnostic agent to remain in circulation and offers better targeting of the agent in vivo.

The preferred surfactant system of mPEG-DSPE (2000) may be used with the organic compounds described in U.S. patent application Ser. No. 10/703,395 previously incorporated by reference and from which priority is claimed. The preferred surfactant system may also be used with diagnostic agents and other organic compounds previously described. In addition, the preferred surfactant system may be employed in other drug delivery vehicles such as micelles, liposomes, nanocapsules, emulsions, cubosomes, hexasomes, and microemulsions.

In a preferred method of preparing nanoparticles with the surfactant system of the present invention, the therapeutic agent is combined with a solvent of the type described above, such as, but not limited to NMP, to provide a first solvent solution. A second solvent solution including Poloxamer 188, the conjugated polymer/phospholipid mPEG-DSPE(2000) and, for example, a tonicity adjuster, such as sucrose, is separately prepared. The solutions are separately filtered. The first solvent solution is added to the second solvent solution, yielding a pre-suspension of microprecipitated agent coated with mPEG-DSPE(2000) and Poloxamer 188. The presuspension may then be subjected to an energy-addition step, as described above.

As demonstrated below, compositions of nanoparticles with the preferred surfactant system of a polyoxyethylene/polyoxypropylene block copolymer (e.g., Poloxamer) and conjugated phospholipid provide, in many respects, improved properties when compared to nanoparticles including only one of either the block copolymer or conjugated phospholipid. The improved properties typically include less aggregation and a smaller mean particle size, under normal as well as stressed conditions. Examples of stressed conditions include, but are not limited to, thermal cycling, repeated freeze-thaw cycling, agitation, and centrifugation. Stress testing methods for particles are well known in the art. Typical stress testing methods are described in detail in Novel Injectable Formulations of Insoluble Drugs, Pace et al., Pharm Tech, March 1999, pg 116-134. In addition, nanoparticles with the preferred surfactant system are less prone to scavenging by the RES of the liver, as compared to surfactant systems that do not include peglyated amphiphiles.

Example 1A: Microprecipitation and Homogenization Processes for Making Paclitaxel Particles with mPEG-DSPE/Poloxamer Surfactant System Example 1A: A solution of paclitaxel in NMP was precipitated in a surfactant solution containing 0.5% poloxamer 188 and 0.05% mPEG-DSPE (2000) (with 2% glycerin as a tonicity agent), at low temperature (<10° C.). The total suspension volume was 10 mL, with a drug concentration of 1% (w/v). High pressure homogenization was carried out immediately after precipitation, at a pressure of ~25,000 psi at a temperature of 40° C. After homogenization (20 minutes), particle size of the suspension was examined using light scattering. Mean particle size was 186 nm.

Example 1B

A solution of paclitaxel in NMP was precipitated in a surfactant solution containing 0.5% w/v poloxamer 188 and 0.05% w/v mPEG-DSPE (2000) (with 2% w/v glycerin as a tonicity agent), at low temperature (<10° C.). The total suspension volume was 20 mL, with a drug concentration of 1% (w/v). High pressure homogenization was carried out immediately after precipitation, at a pressure of ~25,000 psi at a temperature of 40° C. After 30 minutes homogenization, particle size of the suspension was examined using light scattering. Mean particle size was 204 nm.

Example 1C

A solution of paclitaxel in NMP was precipitated in a surfactant solution containing 0.5% poloxamer 188 and 0.05% mPEG-DSPE (2000) (with 2% glycerin as a tonicity agent), at low temperature (<10° C.). The total suspension volume was 10 mL, with a drug concentration of 1% (w/v). High pressure homogenization was carried out immediately after precipitation, at a pressure of ~25,000 psi at a temperature of 70° C. After homogenization, particle size of the suspension was examined using light scattering. Mean particle size was 158 nm. About 45% of particles were under 150 nm.

Example 1D

A solution of paclitaxel in NMP was precipitated in a surfactant solution containing 0.05% mPEG-DSPE (2000) (with 2% glycerin as a tonicity agent), at low temperature (<10° C.). The total suspension volume was 10 mL, with a drug concentration of 1% (w/v). High pressure homogenization was carried out immediately after precipitation, at a pressure of ~25,000 psi at a temperature of 40° C. After homogenization, particle size of the suspension was examined using light scattering. Mean particle size was 244 nm.

Figure 3:
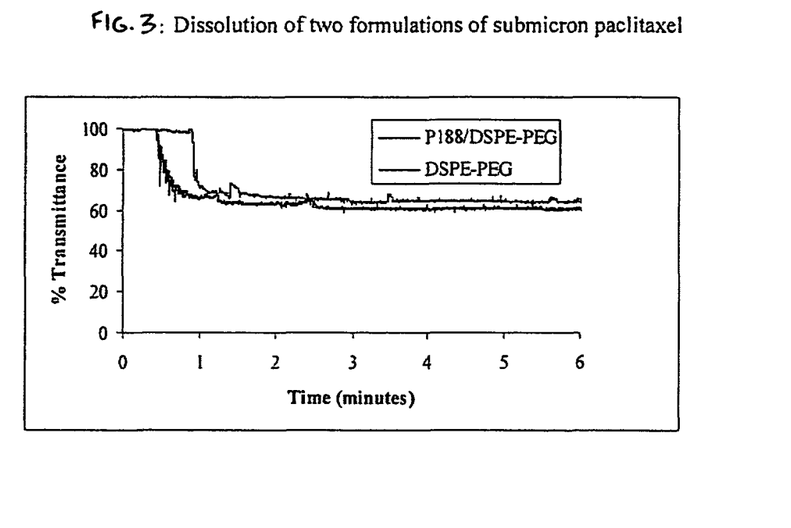
FIG. 3 shows the dissolution of two formulations of submicron (paclitaxel) particles with the mPEG-DSPE/Poloxamer surfactant system of the present invention.

Example 2: Dissolution Characteristics of Paclitaxel Submicron Particles with mPEG-DSPE/Poloxamer Surfactant System Two formulations of paclitaxel particles prepared by the methods described in Example 1 were tested for their solubility by dissolution kinetics using % transmission at 400 nm as a measure for dissolution. The particles are not soluble if % transmission does not return to 100% after addition of suspension. One formulation contains the surface modifiers poloxamer 188 (P188) and mPEG-DSPE (2000). The other formulation contains the surface modifier of mPEG-DSPE (2000) only. The results are shown in FIG. 3. In both cases, % transmission did not rise after the initial drop to about 60%, indicating that the particles do not dissolve.

Figure 4:
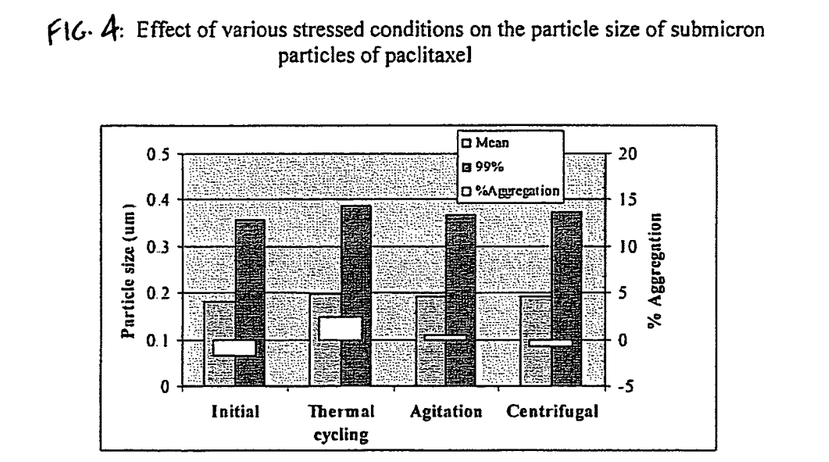
FIG. 4 shows the effect of various stressed conditions on the particle size of submicron (paclitaxel) particles with the mPEG-DSPE/Poloxamer surfactant system of the present invention.
Figure 5:
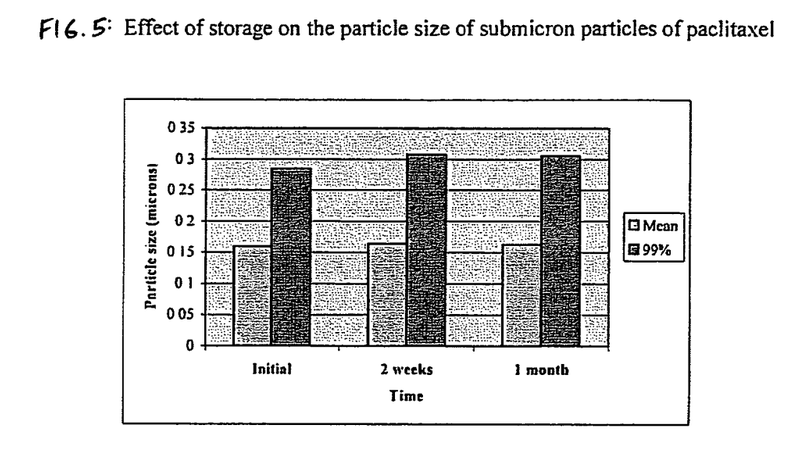
FIG. 5 shows the effect of storage on the particle size of submicron (paclitaxel) particles with the mPEG-DSPE/Poloxamer surfactant system of the present invention.

Example 3: Stability of Paclitaxel Submicron Particles with Mpeg-DSPE/Poloxamer Surfactant System Under Stressed Conditions and Upon Storage Stability of the submicron paclitaxel particles prepared in Example 1A was tested using accelerated stress testing as well as storage at 5° C. for one month. As shown in FIGS. 4 and 5, the mean particle size and the 99th percentile both remained virtually unchanged. No aggregation was observed for the formulation either, even after all the stress tests. Aggregation was estimated by measuring particle size before and after 1 minute sonication and comparing the difference via the following equation:

$$\% \text{ Aggregation} = \frac{(P_{99} - P_{99S}) \times 100}{P_{99S}}$$

where P99 represents $99^{th}$ percentile of the particle size distribution before sonication, and P99S represents $99^{th}$ percentile of the particle size distribution after sonication.

Figure 6:
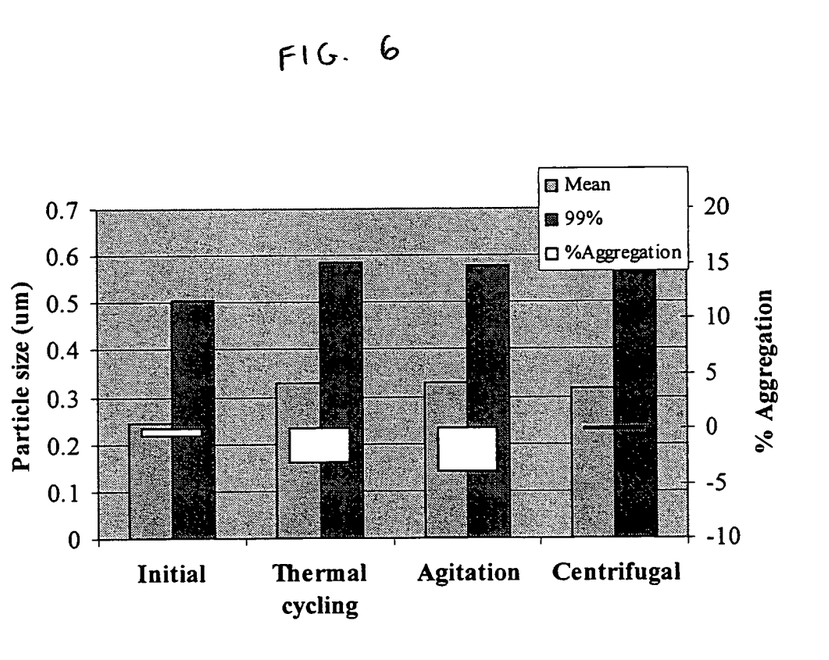
FIG. 6 shows the effects of various stress conditions on the particle size of submicron (paclitaxel) particles with mPEG-DSPE surfactant only.

The above results and those shown in FIG. 4 were compared with those for nanoparticulate compositions including only DSPE-PEG 2000 (i.e., no Poloxamer), as reported in FIG. 6. As shown in FIG. 6, increased aggregation was observed when particles including only DSPE-PEG 2000 were subjected to thermal cycling, agitation or centrifugation.

Example 4: Stability of Itraconazole Nanoparticles with Poloxamer 188/mPEG DSPE(2000) Surfactant System Under Stressed Conditions and Upon Storage A surfactant solution containing 0.1% Poloxamer 188, 0.08% mPEG-DSPE(2000), and 9.25% sucrose was prepared. 0.505 g of itraconazole was added to the surfactant solution. The mixture was subjected to high shear mixing for 4 minutes using an Ultra-Turrax T8 mixer (setting 6) to form a presuspension. The presuspension was then homogenized in a C5 Avestin homogenizer for 8 minutes at 25,000 psi to form a nanosuspension. The mean particle size of the nanosuspension was 0.695 μm and 99% of the particles less than 1.651 μm.

Figure 7:
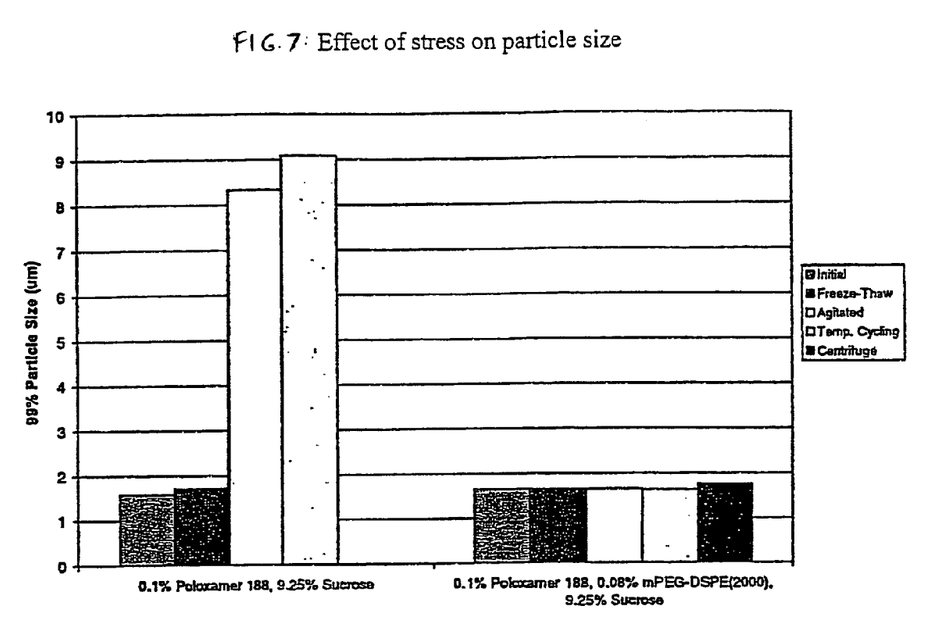
FIG. 7 shows the effects of stress on the particle size of nanoparticles of the drug itraconazole with the surfactant system of the present invention and a poloxamer surfactant only.
Figure 8:
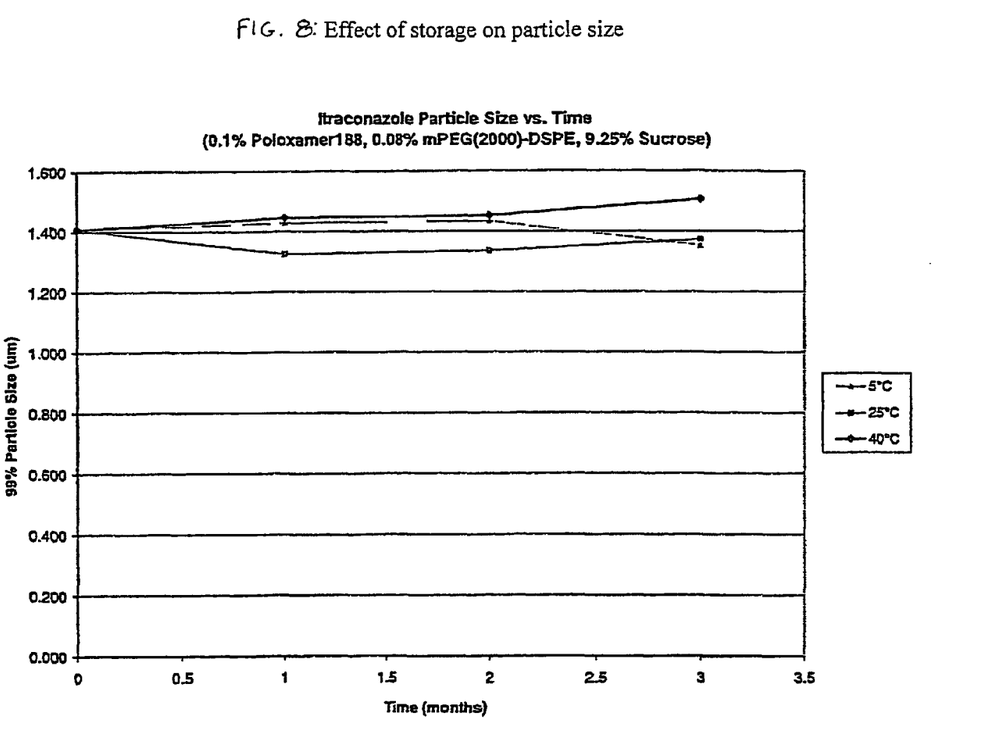
FIG. 8 shows the long-term stability of nanoparticles made with the surfactant system of the present invention.

This sample was subjected to various stress tests, including temperature cycling, centrifugation, agitation, and freezing. The results of the stress tests are shown in FIG. 7. Data is also included showing the effect of stress on nanoparticles treated with a surfactant solution including 0.1% Poloxamer 188 and 9.25% sucrose, but without mPEG-DSPE(2000) formulation. As seen in FIG. 7, no significant particle size increase or caking was found in the nanoparticles treated with the Poloxamer 188/mPEG-DSPE(2000) combination. In addition, this sample was placed on long-term stability at 5° C., 25° C., and 40° C. The results of the 3-month interval are shown in FIG. 8. As seen in FIG. 7, no significant increase in particle size was observed.

While specific embodiments have been illustrated and described, numerous modifications come to mind without departing from the spirit of the invention and the scope of protection is only limited by the scope of the accompanying claims.

What is claimed:

1. A liquid suspension comprising solid particles of an organic compound and surfactants associated therewith, said surfactants consisting of (a) block copolymer of polyoxyethylene and polyoxypropylene and (b) an amphiphilic compound conjugated with a hydrophilic polymer, wherein the block copolymer and said conjugated amphiphilic compound are provided in the liquid suspension in a weight ratio greater than 1:1, said block copolymer is $HO(CH_2CH_2O)_{80}(C_3H_6O)_{27}(CH_2CH_2O)_{80}H$, said amphiphilic compound is 1,2-Distearoyl-sn-glycero-3-phophoethanolamine, said hydrophilic polymer is a polyethylene glycol polymer having a weight average molecular weight between 200 Da and 50,000 Da, the solid particles having a mean particle size from about 50 nm to about 1 µm, the organic compound has a solubility in water of less than 1 mg/mL, the suspension comprises approximately 0.1% to 1.0% (w/v) of the surfactants, and the organic compound is a therapeutic agent other than a biologic.

2. The liquid suspension of claim 1 wherein said polyethylene glycol polymer is selected from the group consisting of PEG 2000, PEG 3000, and PEG 5000.

3. The liquid suspension of claim 1 wherein said amphiphilic compound conjugated with said hydrophilic polymer is 1,2-Distearoyl-sn-glycero-3-phosphoethanolamine-N-[methoxy(polyethyleneglycol)-2000].

4. The liquid suspension of claim 1 wherein said two surfactants consist of the combination of $HO(CH_2CH_2O)_{80}(C_3H_6O)_{27}(CH_2CH_2O)_{80}H$ and 1,2-Distearoyl-sn-glycero-3-phosphoethanolamine-N-[methoxy(polyethyleneglycol)-2000].

5. The composition of claim 1 wherein said surfactants include approximately 60%-80% (w/w) of said block copolymer and approximately 20%-40% (w/w) of said amphiphilic compound conjugated with a hydrophilic polymer, based on the total weight of the surfactant.

6. A method for making a liquid suspension comprising solid particles of an organic compound, said particles having a mean particle size of about 50 nm to about 1 µm, comprising: dissolving an organic compound in a water miscible solvent to form a first solution; preparing an aqueous solution comprising surfactants, wherein said surfactants consist of a block copolymer of polyoxyethylene and polyoxypropylene and a hydrophilic polymer conjugated with phospholipids wherein the block copolymer and the hydrophilic polymer are provided in a weight ratio greater than 1:1; adding said first solution to said aqueous solution to form a presuspension; and adding energy to said presuspension to provide a liquid suspension of the particles, wherein the organic compound comprises a therapeutic agent other than a biologic, the block copolymer is $HO(CH_2CH_2O)_{80}(C_3H_6O)_{27}(CH_2CH_2O)_{80}H$, said phospholipid is 1,2-Distearoyl-sn-glycero-3-phosphoethanolamine, and said hydrophilic polymer is a polyethylene glycol polymer with a molecular weight of between 200 Da and 50,000 Da; wherein the liquid suspension comprises approximately 0.1% to 1.0% (w/v) of said two surfactants.

7. The method of claim 6 wherein said phospholipid conjugated with said hydrophilic polymer is 1,2-Distearoyl-sn-glycero-3-phosphoethanolamine-N-[methoxy(polyethyleneglycol)-2000].

8. The method of claim 6, wherein the liquid suspension comprises approximately 0.5%-20% (w/v) of said organic compound.

9. A method for making solid particles of an organic compound, the particles having mean particle size of about 50 nm to about 1 µm, comprising: adding an organic compound and surfactants, said surfactants consisting of a block copolymer of polyoxyethylene and polyoxypropylene and a hydrophilic polymer conjugated with a phospholipid wherein the block copolymer and the hydrophilic polymer are provided in a weight ratio greater than 1:1, to a milling apparatus and forming a mixture; adding a suitable grinding media to the milling apparatus; and milling the mixture in the presence of the grinding media, wherein the organic compound comprises a therapeutic agent other than a biologic, the block copolymer is $HO(CH_2CH_2O)_{80}(C_3H_6O)_{27}(CH_2CH_2O)_{80}H$, said phospholipid is 1,2-Distearoyl-sn-glycero-3-phosphoethanolamine, and said hydrophilic polymer is a polyethylene glycol polymer with a molecular weight of between 200 Da and 50,000 Da; wherein the mixture of organic compound and surfactants comprises approximately 0.1% to 1.0% (w/v) of said two surfactants.

10. The method of claim 9, wherein the mixture of organic compound and surfactants comprising approximately 0.5%-20% (w/v) of said organic compound.

11. A method of administering to a subject an effective amount of a composition comprising a liquid suspension of solid particles including an organic compound associated with surfactants, the particles having a mean particle size of about 50 nm to about 1 µm, wherein the surfactants consist of (a) a block copolymer of polyoxyethylene and polyoxypropylene and (b) an amphiphilic compound conjugated with a hydrophilic polymer and the block copolymer and said conjugated amphiphilic compound are provided in a weight ratio greater than 1:1, and wherein the organic compound comprises a therapeutic agent other than a biologic, the block copolymer is $HO(CH_2CH_2O)_{80}(C_3H_6O)_{27}(CH_2CH_2O)_{80}H$, said phospholipid is 1,2-Distearoyl-sn-glycero-3-phosphoethanolamine, and said hydrophilic polymer is a polyethylene glycol polymer with a molecular weight of between 200 Da and 50,000 Da; wherein the liquid suspension comprises approximately 0.1% to 1.0% (w/v) of said two surfactants.

12. The method of claim 11, wherein said composition comprises approximately 0.5%-20% (w/v) of said organic compound.

13. The liquid suspension of claim 1, wherein the organic compound is paclitaxel.

14. The liquid suspension of claim 1, wherein the organic compound is selected from the group consisting of insoluble antifungal therapeutics, insoluble anticancer therapeutics, and combinations thereof.

15. The liquid suspension of claim 1, wherein the organic compound is paclitaxel and said two surfactants consist of the combination of $HO(CH_2CH_2O)_{80}(C_3H_6O)_{27}(CH_2CH_2O)_{80}H$ and 1,2-Distearoyl-sn-glycero-3-phosphoethanolamine-N-[methoxy(polyethyleneglycol)-2000].

* * * * *

UNITED STATES PATENT AND TRADEMARK OFFICE
CERTIFICATE OF CORRECTION

PATENT NO. : 9,700,866 B2
APPLICATION NO. : 11/224633
DATED : July 11, 2017
INVENTOR(S) : Mahesh Chaubal et al.

It is certified that error appears in the above-identified patent and that said Letters Patent is hereby corrected as shown below:

In the Claims

At Column 13, Line 21, "The composition of claim" should be -- The liquid suspension of claim --.

At Column 14, Line 20, "comprising" should be -- comprises --.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*